United States Patent
Meca

(10) Patent No.: US 10,125,122 B2
(45) Date of Patent: Nov. 13, 2018

(54) METHOD FOR PREPARING METHYL (Z)-3-[[[4-[METHYL[2-(4-METHYL-1-PIPERAZINYL)ACETYL]AMINO]PHENYL] AMINO]PHENYLMETHYLENE)OXINDOLE-6-CARBOXYLATE (INTEDANIB, NINTEDANIB)

(71) Applicant: Zentiva k.s., Prague (CZ)

(72) Inventor: Ludek Meca, Dobra (CZ)

(73) Assignee: Zentiva k.s., Prague (CZ)

( * ) Notice: Subject to any disclaimer, the term of this patent is extended or adjusted under 35 U.S.C. 154(b) by 0 days.

(21) Appl. No.: 15/748,196

(22) PCT Filed: Jul. 28, 2016

(86) PCT No.: PCT/CZ2016/000083
§ 371 (c)(1),
(2) Date: Jan. 29, 2018

(87) PCT Pub. No.: WO2017/016530
PCT Pub. Date: Feb. 2, 2017

(65) Prior Publication Data
US 2018/0215735 A1    Aug. 2, 2018

(30) Foreign Application Priority Data

Jul. 29, 2015    (CZ) .................................... 2015-527

(51) Int. Cl.
*C07D 403/02*    (2006.01)
*C07D 403/12*    (2006.01)
*C07B 43/04*    (2006.01)

(52) U.S. Cl.
CPC ............ *C07D 403/12* (2013.01); *C07B 43/04* (2013.01)

(58) Field of Classification Search
CPC .................................................. C07D 403/02
USPC ....................................................... 544/373
See application file for complete search history.

(56) References Cited

FOREIGN PATENT DOCUMENTS

| WO | WO 2009071523 | 6/2009 |
|---|---|---|
| WO | WO 2012/068441 A2 | 5/2012 |

OTHER PUBLICATIONS

Roth et al; J.Med.Chem., vol. 52, 2009, pp. 4466-4480.
"Process for the Preparation of Indolinone Compound: IPCOM000241006D", IP Com Journal, IP Com Inc., West Henrietta, NY, US; vol. 15, No. 4A, Jan. 1, 2015, pp. 7-8.
Xu R et al; "Design, Synthesis and biological evaluation of deuterated nintedanib for improving pharmacokinetic properties"; Journal of Labelled Compounds and Radiopharmaceuticals, John Wiley, Chichester, GB; vol. 58, No. 7, Jun. 1, 2015, pp. 308-312.
International Search Report (ISR) issued for WO2017016530 dated Sep. 29, 2016.

*Primary Examiner* — Douglas M Willis
(74) *Attorney, Agent, or Firm* — Pearl Cohen Zedek Latzer Baratz LLP

(57) ABSTRACT

The invention relates to a method of synthesizing methyl (Z)-3-[[4-[methyl[2-(4-methyl-1-piperazinyl)acetyl]amino] phenyl] amino]phenylmethylene)-oxindole-6-carboxylate of formula (1), known under the generic name of intedanib or nintedanib. The present method comprises a) a reaction of methyl oxindole-6-carboxylate with acetic anhydride at a temperature of 130-140° C., providing methyl 1-acetyl-oxindole-6-carboxylate; b) a reaction of methyl 1-acetyl-oxindole-6-carboxylate of with trimethyl orthobenzoate and acetic anhydride in the presence of toluene, providing methyl (E)-1-acetyl-3-(methoxyphenylmethylene)-oxindole-6-carboxylate; c) a reaction (E)-1-acetyl-3-(methoxyphenylmethylene)-oxindole-6-carboxylate with N-(4-aminophenyl)-N,4-dimethyl-1-piperazine acetamide and subsequently with an alkali hydroxide or alkali alkoxide in methanol or ethanol without isolation of the intermediate, providing methyl (Z)-3-[[4-[methyl[2-(4-methyl-1-piperazinyl)acetyl]amino]phenyl] amino]phenylmethylene)-oxindole-6-carboxylate, wherein the reaction is conducted at a temperature of 50 to 100° C. (1).

(1)

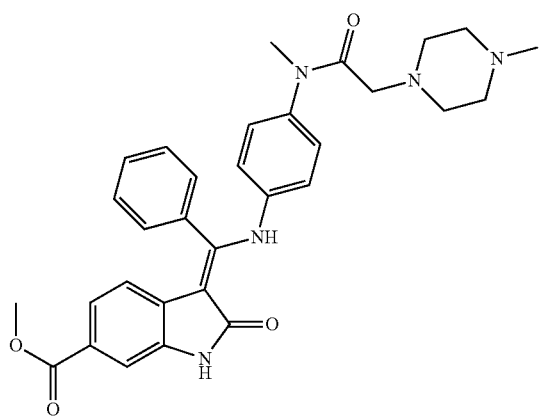

3 Claims, No Drawings

METHOD FOR PREPARING METHYL (Z)-3-[[[4-[METHYL[2-(4-METHYL-1-PIPERAZINYL)ACETYL]AMINO]PHENYL]AMINO]PHENYLMETHYLENE)OXINDOLE-6-CARBOXYLATE (INTEDANIB, NINTEDANIB)

CROSS-REFERENCE TO RELATED APPLICATIONS

This application is a National Phase Application of PCT International Application No. PCT/CZ2016/000083, International Filing Date Jul. 28, 2016, claiming priority of Czech Republic Patent Application No. PV 2015-527, filed Jul. 29, 2015, both of which are hereby incorporated in their entirety.

FIELD OF THE INVENTION

The invention relates to a method of synthesizing methyl (Z)-3-[[4-[methyl[2-(4-methyl-1-piperazinyl)acetyl]amino]phenyl]amino]phenylmethylene)-oxindole-6-carboxylate of formula 1, known under the generic name of intedanib or nintedanib.

(1)

Intedanib is a combined inhibitor of the vascular endothelial growth factor receptor (VEGFR), fibroblast growth factor receptor (FGFR) and platelet derived growth factor receptor (PDGFR) that is used as a selective antagonist of the protein thyrosine kinase receptor. It is designed for the treatment of idiopathic pulmonary fibrosis (IPF) and in combination with other active ingredients also for the treatment of certain types of cancer. A combination of intedanib with docetaxel is designed for the treatment of non-small cell lung cancer (NSCLC).

BACKGROUND OF THE INVENTION

Preparation of intedanib of formula 1 is first described by the patent application WO0127081 (Scheme 1).

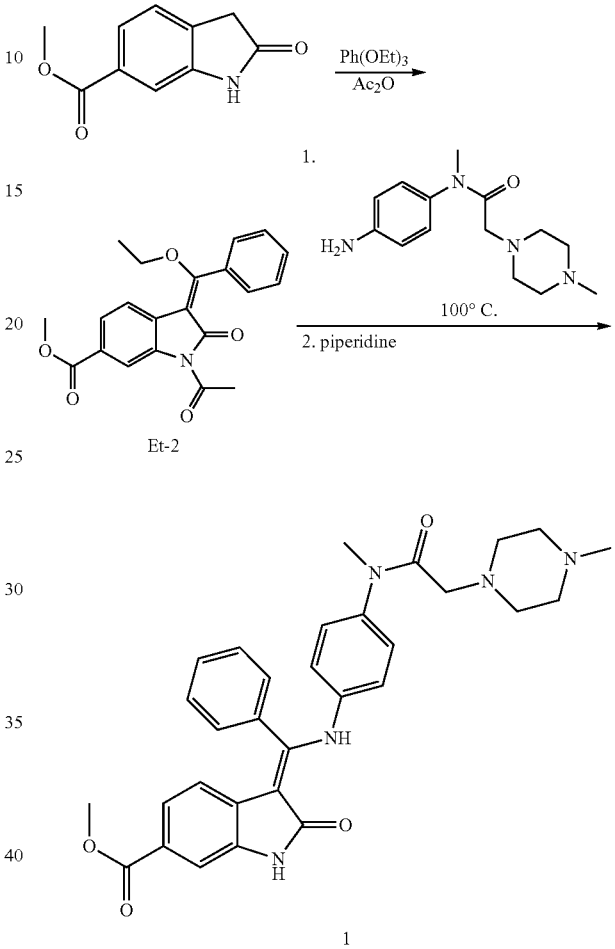

In this synthesis, methyl oxindole-6-carboxylate is converted to methyl (E)-1-acetyl-3-(ethoxyphenylmethylene)-oxindole-6-carboxylate of formula Et-2 with the yield of 61%. The compound Et-2 subsequently reacts with N-(4-aminophenyl)-N,4-dimethyl-1-piperazine acetamide and then, without isolation of the intermediate, with piperidine, producing intedanib of formula 1. The yield of this reaction step is not mentioned.

A modification of the above mentioned preparation of intedanib 1 was published in *J. Med. Chem.* 2009, 52, 4466-4480 (Scheme 2).

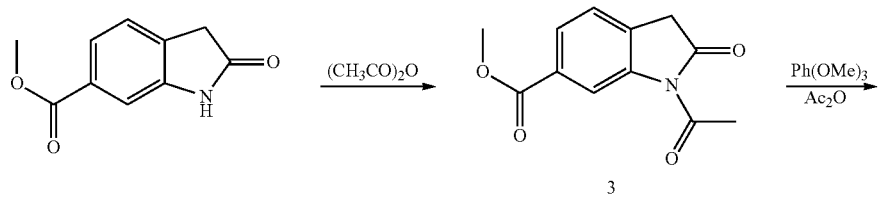

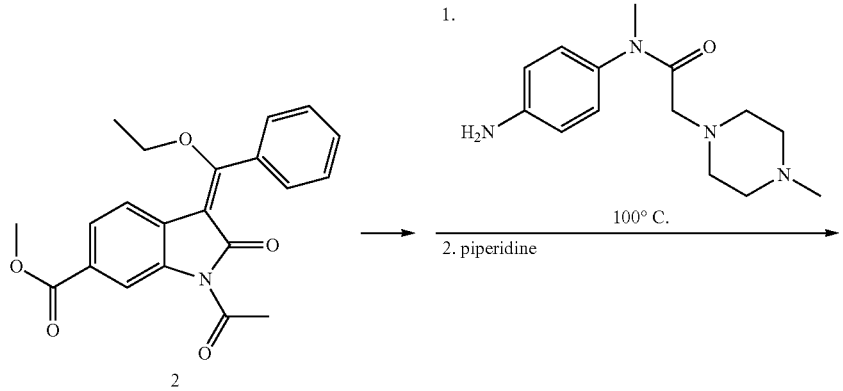

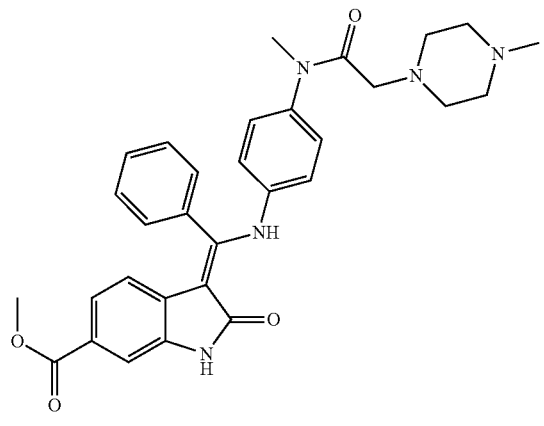

There, methyl oxindole-6-carboxylate is first converted to methyl 1-acetyl-oxindole-6-carboxylate of formula 3 with the yield of 73%. Intermediate 3 is then converted to methyl (E)-1-acetyl-3-(methoxyphenylmethylene)-oxindole-6-carboxylate of formula 2 without the yield being mentioned. Compound 2 subsequently reacts with N-(4-aminophenyl)-N,4-dimethyl-1-piperazine acetamide and then, without isolation of the intermediate, with piperidine, producing intedanib of formula 1. The yield of this reaction step is 77%. A weak point of the above mentioned synthesis is a relatively low yield of compound 3 in the first step. A significant drawback of the above mentioned synthesis is the use of the toxic dimethyl formamide as the solvent and of the toxic piperidine as the base in the last step.

A preparation method of intedanib of formula 1 suitable for industrial production is described in the patent application WO2009071523 (Scheme 3).

Scheme 3

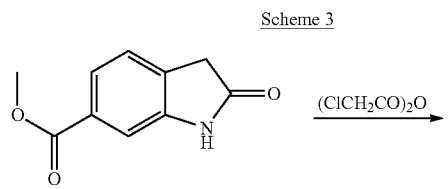

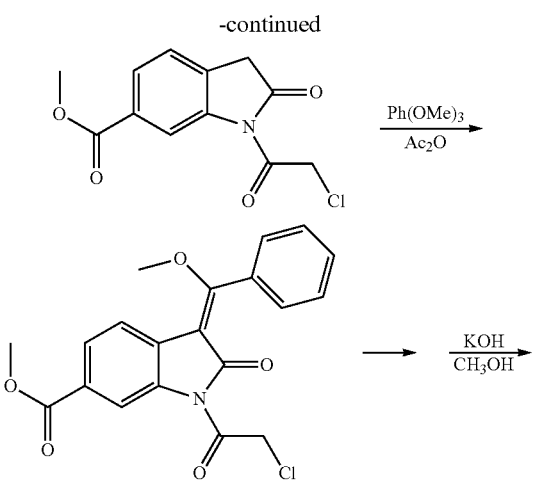

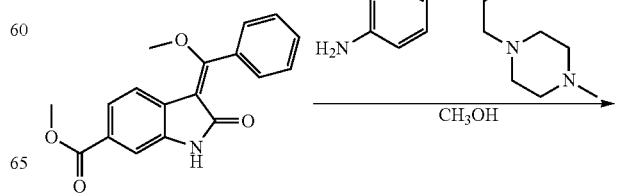

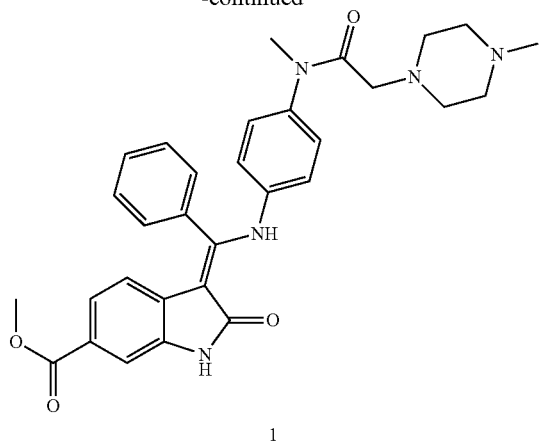

(1)

Methyl oxindole-6-carboxylate is first converted to methyl 1-chloroacetyl-oxindole-6-carboxylate with the yield of 93.5%. It is followed by a reaction of this compound with trimethyl orthobenzoate, producing methyl (E)-1-chloroacetyl-3-(methoxyphenylmethylene)-oxindole-6-carboxylate with the yield of 91.7%. Then, the chloroacetyl group is removed, producing methyl (E)-3-(methoxyphenylmethylene)-oxindole-6-carboxylate with the yield of 94.6% and, finally, a reaction of this compound with N-(4-aminophenyl)-N,4-dimethyl-1-piperazine acetamide provides intedanib of formula 1 with the yield of 89%. A weak point of the above mentioned synthesis is the use of the expensive chloroacetanhydride as the acylating agent in the first step. A considerable disadvantage of the above mentioned synthesis is the formation of the toxic methyl chloroacetate as a side product in the third step.

SUMMARY OF THE INVENTION

The invention provides a method for preparing methyl (Z)-3-[[4-[methyl[2-(4-methyl-1-piperazinyl)acetyl]amino]phenyl]amino]phenylmethylene)-oxindole-6-carboxylate of formula 1, comprising:

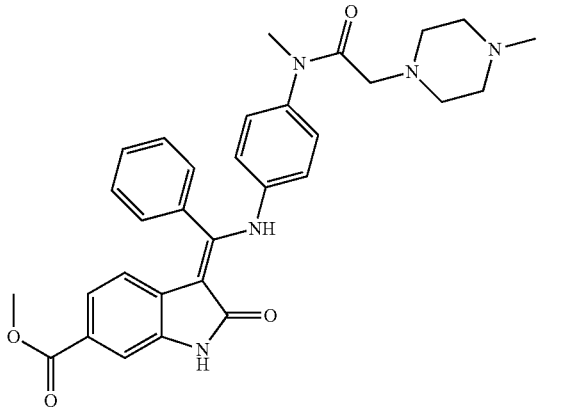

(1)

a) a reaction of methyl oxindole-6-carboxylate with acetic anhydride at a temperature of 130 to 140° C., providing methyl 1-acetyl-oxindole-6-carboxylate of formula 3

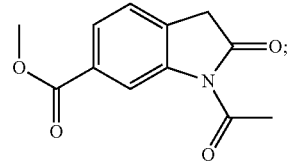

(3)

b) a reaction of methyl 1-acetyl-oxindole-6-carboxylate of formula 3 with trimethyl orthobenzoate and acetic anhydride in the presence of toluene, providing methyl (E)-1-acetyl-3-(methoxyphenylmethylene)-oxindole-6-carboxylate of formula 2

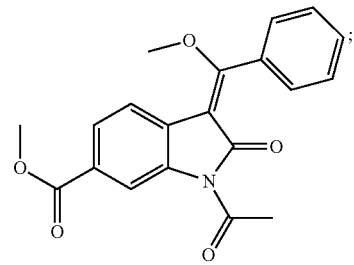

(2)

c) a reaction (E)-1-acetyl-3-(methoxyphenylmethylene)-oxindole-6-carboxylate of formula 2 with N-(4-aminophenyl)-N,4-dimethyl-1-piperazine acetamide and subsequently with a suitable base in a suitable solvent, without isolation of the intermediate, providing methyl (Z)-3-[[4-[methyl[2-(4-methyl-1-piperazinyl)acetyl]amino]phenyl]amino]phenylmethylene)-oxindole-6-carboxylate of formula 1, wherein an alkali hydroxide or alkali alkoxide is used as the suitable base, preferably potassium hydroxide, potassium tert-butoxide or sodium ethoxide. Solvents that are suitable for this reaction are C1 to C4 aliphatic alcohols, ethers, cyclohexane, toluene, xylene and their mixtures. Preferably, a solvent from the group of methanol, ethanol, tetrahydrofuran, tert-butyl methyl ether, dioxane, 1,2-dimethoxyethane, bis(2-methoxyethyl)ether and their mixtures can be used.

DETAILED DESCRIPTION OF THE INVENTION

The invention provides a method for preparing intedanib of formula 1 from methyl oxindole-6-carboxylate, wherein methyl oxindole-6-carboxylate is first converted to methyl 1-acetyl-oxindole-6-carboxylate of formula 3, methyl (E)-1-acetyl-3-(methoxyphenylmethylene)-oxindole-6-carboxylate of formula 2 is prepared from compound 3, and, finally, compound 2 is converted to intedanib of formula 1 (Scheme 4).

Scheme 4

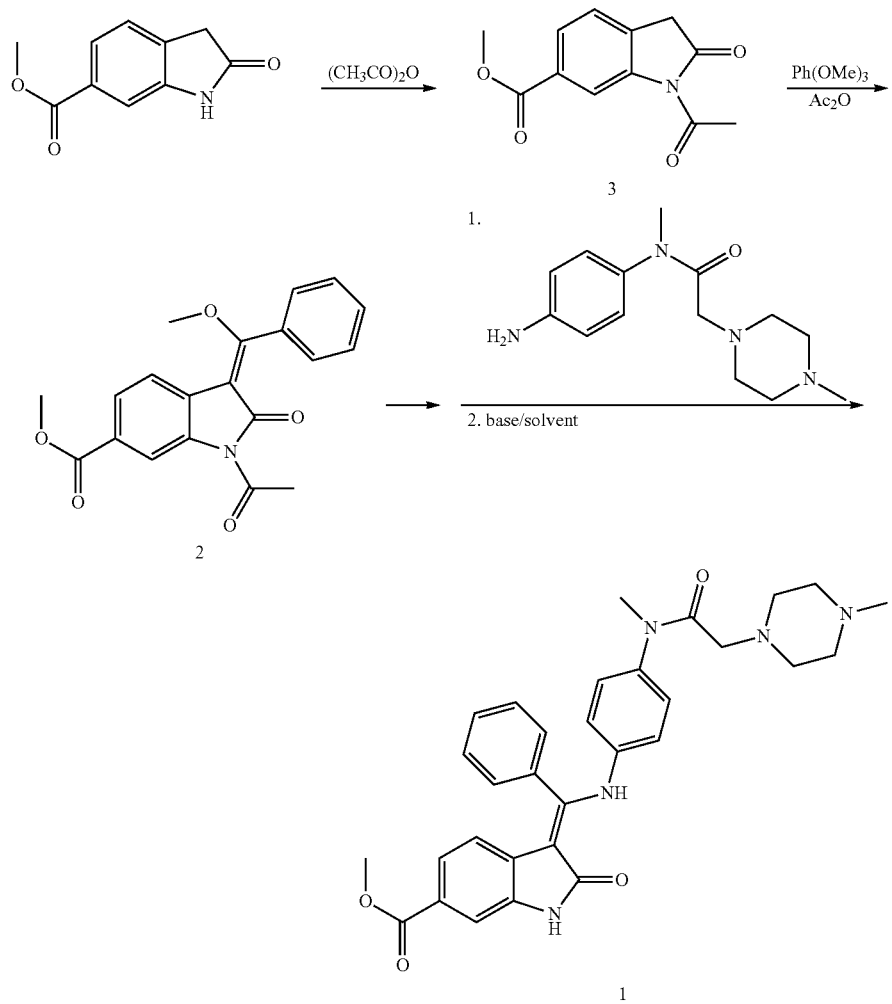

The preparation of methyl 1-acetyl-oxindole-6-carboxylate of formula 3 is carried out by the treatment with acetic anhydride of methyl oxindole-6-carboxylate. A high yield of methyl 1-acetyl-oxindole-6-carboxylate of formula 3 has been observed (87%).

The preparation of compound 2 is carried out by the treatment with acetic anhydride and trimethyl orthobenzoate of methyl 1-acetyl-oxindole-6-carboxylate of formula 3. A high yield of methyl (E)-1-acetyl-3-(methoxyphenylmethylene)-oxindole-6-carboxylate of formula 2 has been observed (83 to 85%).

The preparation of intedanib of formula 1 is carried out by the treatment with N-(4-aminophenyl)-N,4-dimethyl-1-piperazine acetamide of methyl (E)-1-acetyl-3-(methoxyphenylmethylene)-oxindole-6-carboxylate of formula 2 and subsequent reaction with a suitable base in a suitable solvent without isolation of the intermediate.

It has been observed that the reaction provides the desired product of formula 1 in a surprisingly high yield (88 to 90%) and chemical purity (HPLC purity 99.80 to 99.86%). Bases that are suitable for the reaction are alkali hydroxides and alkali alkoxides. Advantageously, potassium hydroxide, potassium tert-butoxide or sodium ethoxide can be used.

Solvents that are suitable for this reaction are C1 to C4 aliphatic alcohols, ethers, cyclohexane, toluene, xylene and their mixtures. Preferably, a solvent from the group of methanol, ethanol, tetrahydrofuran, tert-butyl methyl ether, dioxane, 1,2-dimethoxyethane, bis(2-methoxyethyl)ether and their mixtures can be used.

A suitable temperature for carrying out the reaction is 50 to 100° C.

An advantage of the process of synthesis of intedanib in accordance with the present invention is a high yield of the reaction and high chemical purity as compared to the preparation according to *J. Med. Chem.* 2009, 52, 4466-4480 (mentioning the yield of 77%; without mentioning the purity of intedanib). A considerable weak point of the synthesis according to *J. Med. Chem.* 2009, 52, 4466-4480, is the use of the toxic dimethyl formamide as the solvent and of the toxic piperidine as the base in the last step. In the process of synthesis in accordance with the present invention, the technologically more suitable methanol or ethanol is preferably used as the solvent and, in the last synthetic step, readily available and environment-friendly bases (alkali hydroxides, alkali alkoxides) are used instead of the toxic piperidine. Compared to WO2009071523, the process of synthesis of intedanib in accordance with the present invention is one step shorter, while, instead of the toxic methyl chloroacetate, it provides the non-toxic methyl acetate as a side product. The synthesis is also convenient from the economic point of view as it avoids the use of the expensive chloroacetanhydride as the acylating agent.

EXAMPLES

The HPLC analyses of individual batches of intedanib of formula 1 were conducted with UV detection at 254 nm; column Acquity UPLC BEH C18 1.7 μm; column length 100 mm; inner diameter of the column 2.1 mm; temperature 40° C.; flow rate 0.4 ml/min; mobile phase A: phosphate buffer (1.32 g $(NH_4)_2HPO_4$ dissolved in 1000 ml of water, adjusted to pH 8.5±0.05 with 25% ammonia); mobile phase B: acetonitrile; gradient elution: 83% A+17% B at the beginning and at 0.8 min, 55% A+45% B at 7 min, 30% A+70% B at 12 min and 83% A+17% B at 13 and 14 min. The typical retention time of intedanib 1 under these conditions was 6.9 min.

The starting methyl (E)-1-acetyl-3-(methoxyphenylmethylene)-oxindole-6-carboxylate and N-(4-aminophenyl)-N,4-dimethyl-1-piperazine acetamide were prepared according to G. J. Roth et al. *J. Med. Chem.* 2009, 52, 4466-4480).

Example 1

Preparation of methyl 1-acetyl-oxindole-6-carboxylate of Formula 3

A mixture of methyl oxindole-6-carboxylate (11.47 g) and acetanhydride (32 ml) was stirred at the bath temperature of 138° C.; a clear red solution was produced within 10 min. The reaction mixture was stirred at 138° C. for 6 h, then left to stand at 20° C. for 4 h and the crystallization of the product was completed in 2 h at 10° C. The product was filtered off, washed with petroleum ether and finally with glacial methanol. The yield was 12.15 g (87%) of reddish crystals.

Example 2

Preparation of methyl (E)-1-acetyl-3-(methoxyphenylmethylene)-oxindole-6-carboxylate of Formula 2

A mixture of methyl 1-acetyl-oxindole-6-carboxylate of formula 3 (1.75 g), toluene (5 ml) and acetanhydride (2.5 ml) was stirred in a flask equipped with a small Vigreux column and a distillation adapter at 110° C. for 5 min, producing a turbid orange-red solution. At the temperature of 110° C., trimethyl orthobenzoate (3.1 ml) was added dropwise to the reaction mixture, followed by toluene (3 ml), by means of a syringe fitted with a needle reaching into the flask. The bath temperature was slowly increased to slowly distil the produced methyl acetate. After distilling for 4 h, the bath temperature was 122° C. and the distillate volume was 1.5 ml. The reaction mixture was left to stand at 20° C. for 4 h and the crystallization of the product was completed in 2 h at 10° C. The product was filtered off, washed with toluene and finally with a mixture of toluene and ethyl acetate (1:1). The yield was 2.19 g (83%) of a beige powder.

Example 3

Preparation of methyl (E)-1-acetyl-3-(methoxyphenylmethylene)-oxindole-6-carboxylate of Formula 2

A mixture of methyl 1-acetyl-oxindole-6-carboxylate of formula 3 (7.00 g), toluene (20 ml) and acetanhydride (9.8 ml) was stirred in a flask equipped with a small Vigreux column and a distillation adapter at 110° C. for 5 min, producing a turbid orange-red solution. At the temperature of 110° C., trimethyl orthobenzoate (12.4 ml) was added dropwise to the reaction mixture, followed by toluene (16 ml), by means of a syringe fitted with a needle reaching into the flask. The bath temperature was slowly increased to slowly distil the produced methyl acetate. After distilling for 4 h, the bath temperature was 125° C. and the distillate volume was 6.5 ml. The reaction mixture was left to stand at 20° C. for 4 h and the crystallization of the product was completed in 2 h at 10° C. The product was filtered off, washed with toluene and finally with a mixture of toluene and ethyl acetate (1:1). The yield was 8.94 g (85%) of a beige powder.

Example 4

Preparation of (Z)-3-[[4-[methyl[2-(4-methyl-1-piperazinyl)acetyl]amino]phenyl]amino]phenylmethylene)-oxindole-6-carboxylate (Intedanib) of Formula 1

A mixture of methyl (E)-1-acetyl-3-(methoxyphenylmethylene)-oxindole-6-carboxylate of formula 2 (0.35 g), N-(4-aminophenyl)-N,4-dimethyl-1-piperazine acetamide (0.27 g) and methanol (2.5 ml) was stirred under reflux for 5 h. The bath temperature was reduced to 70° C. and, at this temperature, a solution of KOH (containing 85% of KOH; 0.040 g) in methanol (0.60 ml) was added dropwise. After adding of 0.10 ml of KOH solution the addition was stopped. The reaction mixture was stirred at 70 to 60° C. for 30 min, then it was left to stand at 20° C. for 2 h and the crystallization of the product was completed in 2 h at 10° C. The product was filtered off, washed with glacial methanol twice and air-dried. The yield was 0.47 g (88%) of a yellow powder. HPLC purity 99.81%.

Example 5

Preparation of (Z)-3-[[4-[methyl[2-(4-methyl-1-piperazinyl)acetyl]amino]phenyl]amino]phenylmethylene)-oxindole-6-carboxylate (Intedanib) of Formula 1

A mixture of methyl (E)-1-acetyl-3-(methoxyphenylmethylene)-oxindole-6-carboxylate of formula 2 (7.03 g), N-(4-aminophenyl)-N,4-dimethyl-1-piperazine acetamide (5.30 g) and methanol (50 ml) was stirred under reflux for 5 h. The bath temperature was reduced to 70° C. and, at this temperature, a solution of KOH (containing 85% of KOH; 0.13 g) in methanol (2 ml) was added dropwise. The reaction mixture was stirred at 70 to 60° C. for 30 min, then it was left to stand at 20° C. for 2 h and the crystallization of the product was completed in 2 h at 10° C. The product was filtered off, washed with glacial methanol twice and air-dried. The yield was 9.71 g (90%) of a yellow powder. HPLC purity 99.86%.

Example 6

Preparation of (Z)-3-[[4-[methyl[2-(4-methyl-1-piperazinyl)acetyl]amino]phenyl]amino]phenylmethylene)-oxindole-6-carboxylate (Intedanib) of Formula 1

A mixture of methyl (E)-1-acetyl-3-(methoxyphenylmethylene)-oxindole-6-carboxylate of formula 2 (0.35 g), N-(4-aminophenyl)-N,4-dimethyl-1-piperazine acetamide (0.27 g) and methanol (2.5 ml) was stirred under reflux conditions for 5 h. The bath temperature was reduced to 70° C. and at this temperature a solution of KO$^t$Bu (0.068 g) in methanol (0.60) was added dropwise. After adding of 0.10 ml of KOtBu solution the addition was stopped. The reaction mixture was stirred at 70 to 60° C. for 30 min, then it was left to stand at 20° C. for 2 h and the crystallization of the product was completed in 2 h at 10° C. The product was filtered off, washed with glacial methanol twice and air-dried. The yield was 0.48 g (89%) of a yellow powder. HPLC purity 99.83%.

Example 7

Preparation of (Z)-3-[[4-[methyl[2-(4-methyl-1-piperazinyl)acetyl]amino]phenyl]amino]phenylmethylene)-oxindole-6-carboxylate (Intedanib) of Formula 1

A mixture of methyl (E)-1-acetyl-3-(methoxyphenylmethylene)-oxindole-6-carboxylate of formula 2 (0.35 g), N-(4-aminophenyl)-N,4-dimethyl-1-piperazine acetamide (0.27 g) and ethanol (2.5 ml) was stirred at the bath temperature of 80° C. for 5 h. The bath temperature was reduced to 70° C. and at this temperature a 2% solution of NaOEt in ethanol (0.43 ml) was added dropwise. The reaction mixture was stirred at 70-60° C. for 30 min, then it was left to stand at 20° C. for 2 h and the crystallization of the product was completed in 2 h at 10° C. The product was filtered off, washed with icy ethanol twice and air-dried. The yield was 0.47 g (88%) of a yellow powder. HPLC purity 99.8%.

The invention claimed is:
1. A method for preparing a compound of formula (1):

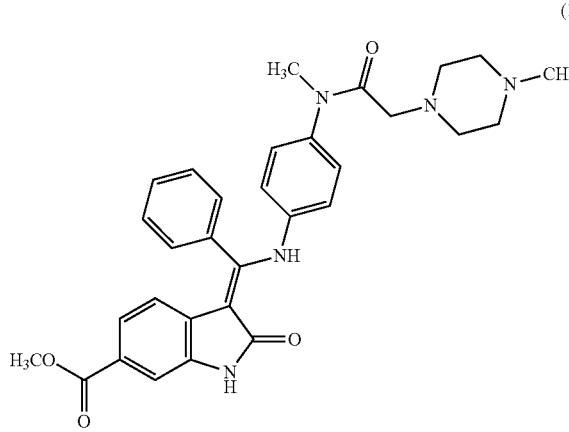

(1)

wherein the method comprises the following steps:
a) reacting a compound of the following formula:

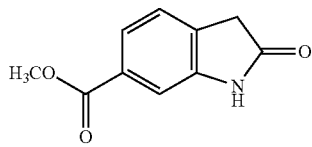 [SMILES: COC(=O)c1ccc2c(c1)NC(=O)C2]

with acetic anhydride at a temperature in the range of 130° C.-140° C., to provide a compound of formula (3):

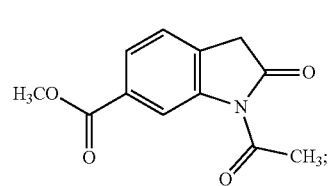

(3)

b) reacting the compound of formula (3) above with a compound of the following formula:

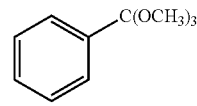

in the presence of acetic anhydride and toluene, to provide a compound of formula (2):

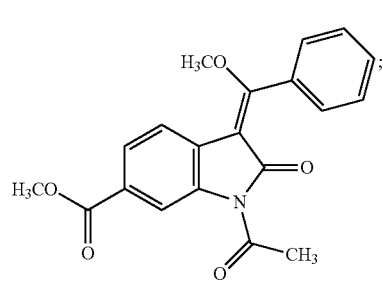

(2)

and c) reacting the compound of formula (2) above with a compound of the following formula:

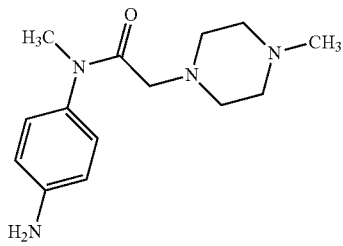 [SMILES: CN1CCN(CC(=O)N(C)c2ccc(N)cc2)CC1]

and subsequently with a base selected from the group consisting of an alkali metal hydroxide and an alkali metal alkoxide in the presence of a solvent selected from the group consisting of methanol and ethanol, at a temperature in the range of 50° C.-100° C. and without isolation of the intermediate, to provide the compound of formula (1) above.

2. The method according to claim 1, wherein the alkali metal hydroxide is potassium hydroxide.

3. The method according to claim 1, wherein the alkali metal alkoxide is selected from the group consisting of sodium ethoxide and potassium tert-butoxide.

* * * * *